(12) United States Patent
Joabsson et al.

(10) Patent No.: US 9,067,190 B2
(45) Date of Patent: Jun. 30, 2015

(54) METHOD FOR LOADING AMPHIPHILE PARTICLES WITH ACTIVE AGENTS

(75) Inventors: Fredrik Joabsson, Lund (SE); Fredrik Tiberg, Lund (SE); Markus Johnsson, Lund (SE)

(73) Assignee: CAMURUS AB, Lund (SE)

( * ) Notice: Subject to any disclaimer, the term of this patent is extended or adjusted under 35 U.S.C. 154(b) by 2316 days.

(21) Appl. No.: 10/566,976

(22) PCT Filed: Aug. 4, 2004

(86) PCT No.: PCT/GB2004/003398
§ 371 (c)(1),
(2), (4) Date: Aug. 9, 2006

(87) PCT Pub. No.: WO2005/014163
PCT Pub. Date: Feb. 17, 2005

(65) Prior Publication Data
US 2007/0110777 A1  May 17, 2007

(30) Foreign Application Priority Data

Aug. 4, 2003 (GB) .................................. 0318244.1
Sep. 23, 2003 (GB) .................................. 0322279.1
Jan. 23, 2004 (GB) .................................. 0401514.5
Jun. 7, 2004 (GB) .................................. 0412671.0

(51) Int. Cl.
*B01J 13/02* (2006.01)
*A61K 9/50* (2006.01)
*B01J 13/00* (2006.01)

(52) U.S. Cl.
CPC ............... *B01J 13/02* (2013.01); *A61K 9/5089* (2013.01); *B01J 13/00* (2013.01)

(58) Field of Classification Search
CPC ........ A61K 9/50; A61K 9/501; A61K 9/5089
USPC .................................. 424/489–493, 496–502
See application file for complete search history.

(56) References Cited

U.S. PATENT DOCUMENTS

| 5,055,228 A | | 10/1991 | Handjani et al. | |
| 5,531,925 A | * | 7/1996 | Landh et al. | 252/299.01 |
| 6,066,328 A | * | 5/2000 | Ribier et al. | 424/401 |
| 6,207,178 B1 | * | 3/2001 | Westesen et al. | 424/405 |

FOREIGN PATENT DOCUMENTS

GB       1 539 625 A       1/1979

OTHER PUBLICATIONS

International Search Report of PCT/GB2004/003398, mailed Nov. 9, 2004.

* cited by examiner

*Primary Examiner* — Michael G Hartley
*Assistant Examiner* — Micah-Paul Young
(74) *Attorney, Agent, or Firm* — Nixon & Vanderhye P.C.

(57) ABSTRACT

The present invention provides a method for the production of amphiphile particles having incorporated therein at least one active agent. The method comprises forming a dispersion of particles comprising at least one amphiphilic structuring agent in a solution of at least one active agent, heating said dispersion to an elevated temperature, followed by cooling to around ambient temperature. The loading provided thereby is typically at least 130% of the loading provided by equilibration of the particles in a solution of active agent. The invention also provides corresponding amphiphile particles.

7 Claims, 5 Drawing Sheets

METHOD FOR LOADING AMPHIPHILE PARTICLES WITH ACTIVE AGENTS

This application is the US national phase of international application PCT/GB2004/003398, filed 4 Aug. 2004, which designated the U.S. and claims priority of GB 0318244.1, filed 4 Aug. 2003; GB 0322279.1, filed 23 Sep. 2003; GB 0401514.5, filed 23 Jan. 2004, and GB 0412671.0, filed 7 Jun. 2004, the entire contents of each of which are hereby incorporated by reference.

The present invention relates to methods for the production of particles suitable for the delivery of active substances. More specifically, the invention relates to methods for the production of amphiphile-based particles containing a high level of active agent.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised. Amphiphile compositions are thus highly suitable for the delivery of compounds of limited aqueous solubility.

The formation of lamellar, non-lamellar and micellar regions in the amphiphile/water, amphiphile/oil and amphiphile/oil/water phase diagrams is a well known phenomenon. Non-lamellar phases include liquid crystalline phases such as the cubic P, cubic D, cubic G and hexagonal phases, which are fluid at the molecular level but show significant long-range order, and the $L_3$ "sponge" phase which comprises a multiply interconnected three-dimensional bi-continuous network of bilayer sheets which lack the long-range order of the liquid crystalline phases. Lamellar phases take the form of bilayer sheets which close to form uni- or multi-lamellar vesicles or liposomes and micellar phases adopt clusters of amphiphile molecules having one group (polar or apolar) directed towards a continuous region and the other group (apolar or polar) directed towards the centre of the cluster.

Depending upon their curvature, the various phases may be described as normal (mean curvature towards the apolar region) or reversed (mean curvature towards the polar region). Where the spontaneous curvature of the lipid system is close to zero, the structures are typically lamellar, such as uni- or multi-lamellar vesicles/liposomes and where the spontaneous curvature is more negative or positive, cubic, hexagonal and micellar phases typically dominate.

The various phases including micellar, lamellar and non-lamellar (e.g. liquid crystalline and $L_3$ phases) are thermodynamically stable systems. That is to say, under suitable conditions they are not simply a meta-stable state that will separate and/or reform into layers, or other phases, but are the thermodynamically stable form of the mixture.

Lamellar, non-lamellar and micellar systems have all been investigated for their properties as carriers and/or excipients for dietary, cosmetic, nutritional, diagnostic and pharmaceutical agents. All phase structures are of value under certain circumstances, the most appropriate depending upon the specific application. Non-lamellar systems in particular are thought to have considerable advantages in terms of their high internal surface area between polar and apolar regions. This has led to considerable investigation of amphiphilic phase structures in controlled-release formulations and for solubilising compounds of relatively low solubility.

As discussed above, a bulk non-lamellar phase is typically a thermodynamically stable system, as are certain dispersed phases such as micelles and vesicles. In addition, the bulk non-lamellar phase may be dispersed in a polar or non-polar solvent to form particles of a non-lamellar (especially liquid crystalline) phase in a bulk solvent. The particles are thus reminiscent of micelles or vesicles but contain a non-lamellar structured core region. Such non-lamellar dispersions allow the advantages of bulk non-lamellar phases to be applied in situations where use of a bulk non-miscible phase would cause problems, such as in parenteral applications. Further control of a compound's release profile may also be achieved by such a dispersion of non-lamellar particles. For example, the particles may be fully (i.e. thermodynamically) stable, or may gradually degrade, thereby providing control over the release profile for active agents formulated therewith.

The formation of dispersions can be spontaneous or as the result of mechanical force such as shearing or ultrasound. Non-lamellar particles are of considerable interest in the delivery of active agents and have been proposed as carriers for many such actives.

A method for the formation of dispersed particles of non-lamellar phase in solvents such as water is described in U.S. Pat. No. 5,531,925. Such particles have a non-lamellar liquid crystalline or $L_3$ interior phase and a lamellar or $L_3$ surface phase and may also contain active ingredients. Methods for the formation of lamellar vesicles and micelles are well known in the art.

Known particles of liquid crystalline or $L_3$ interior phase may be formed by methods such as adding to this phase a solution of surface-phase forming agent, stirring to form a coarse dispersion and fragmenting the resulting mixture.

Cryo-Transmission Electron Microscopy (cryo-TEM) may be used to examine the particle size and phase structure(s) present in a dispersion. In addition, the presence of a liquid crystalline phase in a prospective liquid crystalline material may be examined by use of small-angle X-ray diffraction (SAX), or Nuclear Magnetic Resonance (NMR) spectroscopy studies. The sizes and size distributions of the dispersed particles may be examined by light scattering, particularly by use of laser light scattering or diffraction instruments.

Dispersions containing active ingredients, and particularly those for intravenous administration to the human or animal body, are desirably colloidal. That is, they should be of a particle size no greater than 10 µm, especially no greater than 5 µm and particularly no greater than 1 µm. If particles within the dispersion exceed this size then the dispersion may not be colloidally stable and there is a considerable risk of causing embolism when the preparation is administered intravenously. Furthermore, it is desirable that the distribution of particle sizes be narrow to maximise control over the release of any active agent. Where a particulate composition is to be administered by a method other than intravenously (e.g. orally, intramuscularly, subcutaneously, rectally or by inhalation), then the particles need not necessarily be colloidal but it remains advantageous to provide a well characterised and reproducible particle size distribution in order to control the rate of decomposition of the particles and/or release of the active agents.

The particle size, phase behaviour and active agent loading of a particulate composition should also be stable to storage over a considerable period of time. If the distribution of particle sizes changes significantly then the effective transport rate for composition (e.g. due to diffusion and rate of release of any active agent) may be adversely affected. Similarly, if the loading level or phase behaviour of a composition alters upon storage then the rate of release of active agent will be altered and control over the release profile may be lost.

Of still greater concern is the stability of particle sizes in a colloidal dispersion for intravenous administration. If the particle size distribution of such a dispersion is not stable (e.g. to storage and distribution) then large particles may form over time and be dangerous when administered. Even if not directly dangerous, storage instability can cause significant variability in pharmacokinetics, dynamics and/or efficacy.

Known methods for the formation of dispersed particles of lamellar, micellar and non-lamellar phase are highly effective. Such dispersions are typically pre-formed and subsequently loaded with active agent by equilibrating the dispersion in a solution of active agent.

In general, the level of active agent which can be incorporated by equilibration in aqueous solution is relatively low but has been assumed to be the maximum level which could be stably retained by an amphiphilic composition. To the extent that any additional loading of active agent was even considered possible, it was assumed that this would be greater than the particles could accept when "saturated" and so would be highly unstable.

Obviously, it would be a considerable advantage to be able to load a greater proportion of active agent into an amphiphilic composition. This would increase the dose of active agent which could be delivered in a particular administration volume, would give further control over the release rate and would reduce the quantity of excipient which must be formulated with the active agent. This reduction would, in turn, reduce possible undesirable effects where a lipid of limited biotolerability was needed. Certain surfactants, for example, produce toxic effects at high levels and have a maximum acceptable daily intake of only a few mg per kg body weight. Higher loading would also improve the ease of production, transport and storage due to the lower masses and volumes of excipient required. Furthermore, smaller volumes may be administered in vivo, which is desirable from a practical point of view as well as potentially reducing discomfort on administration (e.g. by injection)

In increasing the loading of an active agent, however, it is highly desirable that the this active agent remain stable in the dispersion and that the particle size and phase behaviour remain stable and/or predictable.

It would thus be a considerable advantage to provide amphiphile compositions, such as dispersions, having a higher loading of active agent than can easily be obtained by simple equilibration. It would be a further distinct advantage if such dispersions were stable to storage in terms of active agent loading, particle size and/or phase behaviour.

The present inventors have now unexpectedly established that by preparing a dispersion of amphiphile particles of appropriate composition in a solution of active agent and heating this dispersion to an elevated temperature for a short period before cooling to around room temperature, the level of active agent loading achieved can be significantly greater than that obtainable by simple equilibration. The present inventors have furthermore established that such particles may be stable to storage in terms of their active agent loading, particle size and/or phase behaviour.

The present invention thus provides a method for the production of (preferably colloidal) amphiphile based particles having incorporated therein at least one active agent, said method comprising forming a dispersion of particles comprising at least one amphiphilic structuring agent in a solution of at least one active agent, heating said particles to an elevated temperature, followed by cooling, preferably to around ambient temperature. Generally, said heating will be to a temperature and for a period sufficient to provide, after cooling, an incorporation of active agent into said particles which is at least 130% of the maximum incorporation provided by equilibrating said particles in a solution of at least one active agent at room temperature or preferably 37° C. for up to 3 days. This heating and cooling method may be carried out once, or as two, three, four or more sequential cycles of heating and cooling.

The present invention further provides a method for increasing the incorporation of at least one active agent into (preferably colloidal) amphiphile particles, above the level achievable by equilibration at room temperature or preferably 37° C., said method comprising forming a dispersion of particles comprising at least one amphiphilic structuring agent in a solution of at least one active agent, heating said particles to an elevated temperature, followed by cooling, preferably to around ambient temperature. Generally, said heating will be to a temperature and for a period sufficient to provide, after cooling, an incorporation of active agent into said particles which is at least 130% of the maximum incorporation provided by equilibrating said particles in a solution of at least one active agent at 37° C. (e.g. for up to 3 days). This heating and cooling method may be carried out once, or as two, three, four or more sequential cycles of heating and cooling.

Evidently, the particles and particle dispersions formed by the methods of the invention have a greater level of active agent incorporation than has previously been achievable. Such particles and all dispersions, creams, gels, powders and compositions thereof are thus new, since these could not be made by previously known methods.

In a further aspect, the present invention therefore provides (preferably colloidal) amphiphile particles comprising at least one structure forming amphiphile and at least one active agent, wherein the incorporation of active agent into said particles is at least 130% of the maximum incorporation provided by incubating equivalent particles not comprising any active agent in a solution of at least one active agent at 37° C. (e.g. for up to 3 days). The particles of the invention may be formed or formable by the methods of the invention.

The heat cycling methods of the invention have surprisingly general application and may be applied to dispersions of many phase structures and for the loading of many active agents. It is obviously desirable that the active agent(s) be stable to the heat treatment method and thus by "active agent" as used herein is intended to indicate a bioactive agent being stable to the heat treatment method and conditions to the extent that no more than 50%, preferably no more than 20% and most preferably no more than 10% of the active agent is destroyed or rendered inactive by the chosen heat treatment loading conditions (for example, those described herein).

The particles of the present invention may be used as a dispersion in a solvent (especially an aqueous solvent), or may be dried and/or formulated as a pharmaceutical composition.

In a further aspect, the present invention thus provides a pharmaceutical composition comprising particles of the present invention, optionally including at least one pharmaceutically tolerable carrier or excipient.

In further aspects, the present invention also provides powders and dispersions comprising particles of the present invention, whether or not these are pharmaceutical compositions and gels, creams, tablets, capsules etc. incorporating such powders or dispersions.

The present invention provides methods by which amphiphilic compositions may be loaded with more active agent than could be achieved by equilibration. It is the surprising finding of the inventors that this elevated level of incorporation remains stable when the particles are cooled (e.g. to 37° C., room temperature, 4° C. or even below). A most surprising aspect of the invention, however, is that the high incorporation of active agent provided by the methods described herein remains stable to storage over a remarkably long period of time.

It was the inventors' initial assumption that the increased loading level observed by the present method was the result of forming a metastable, "supersaturated" type state and that consequently the particles formed would not retain the active agent and would possibly be unstable in terms of particle size and distribution over a short period of time. It was therefore expected that precipitation or separation of the active agent would be observed or that the particle structure would be disrupted to the extent that particles would break, fuse or separate from the dispersion.

At present, no explanation can be offered as to why the particles of and formed by the present invention are stable, particularly in terms of size distribution and to the loss of active agent. It may be, for example, that a metastable "supersaturated" state with a long lifetime is formed or that microscopic drops or crystals of active agent become entrapped within the particles and all of these possible embodiments fall within the scope of the present invention. It is, however, the observation of the inventors that a considerable number of different amphiphile dispersions of varying compositions and phase structures have remained stable for many days with each of a number of active agent incorporated at a level significantly in excess of that achievable by other methods.

In a highly preferred aspect, the present invention thus provides methods and particles of the invention wherein the loaded particles are stable to the loss of active agent for a period of no less than 24 hours at 25° C. Preferably such particles are stable to the loss of active agent when stored in aqueous dispersion at 25° C. for at least 5 days, more preferably at least 2 weeks and most preferably at least 1 month. It is yet more preferable that these periods of stability be shown upon storage at 4° C., 25° C. and 40° C. By "stable" to the loss of active agent is meant that, at the end of the storage period, no less than 90% and preferably no less than 95% of the active agent remains incorporated into the particles, relative to that present 1 hour after the (or the last, if appropriate,) heating and cooling cycle.

The amphiphile based particles of the invention and formed in the loading method of the invention are also preferably stable to storage in terms of their size and size distribution. Such formulations should be essentially stable for periods of at least 24 hours at 25° C. and generally 10 days at room temperature, more typically at least 1 month, preferably at least 3 months and more preferably 6 months or more. In contrast, previously known dispersions of similar average particle size even without the very high active agent loading provided by the present invention may have particle sizes stable for less than 10 days at room temperature.

In one embodiment, a particle size distribution can be considered essentially stable to storage if the average (mode or preferably mean) particle size increases no more than two fold during the storage period. Preferably, the average size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period.

In a highly preferred embodiment, average particle size and particle size distribution width at half-height alter by no more than 10% and remain monomodal on storage for the periods indicated above.

With colloidal formulations, especially for parenteral use, a formulation may be considered stable to storage if no more than 10%, preferably no more than 5%, of particles (by volume) are larger than 10 µm, preferably 8 µm after the storage periods indicated above.

It is particularly-important in the case of colloidal dispersions for use in intravenous or intra-arterial administration that the particle size distribution be stable to storage. A composition containing even a relatively small component of non-colloidal particles may cause embolism, or at least unpredictable rates of release upon administration directly to the blood stream. Similarly, the controlled release of an active agent may be dependent not only upon stable loading but also upon a reliable particle size distribution in a composition. Pharmaceutical, diagnostic and veterinary products are also desirably stable to storage for several months or the cost and availability of the product is significantly adversely affected. The method of the invention thus significantly improves the prospect of an active agent formulated in a dispersion of non-lamellar particles forming a safe and available product with high effectiveness.

The method of the present invention may be used to load suitable active agents into dispersed particles having any formable phase structure (by choice of appropriate compositions). It is preferable, however, that the particles to be loaded are substantially not lamellar particles (i.e. are substantially non-lamellar or micellar) since a greater increase in loading has been observed in such systems. More preferably, the particles to be loaded with (at least one) active agent will substantially be non-lamellar particles such as particles of hexagonal or bicontinuous cubic phase.

In a preferred aspect of the invention, at least 75% (by volume) of the particles to be loaded by the method of the invention will be non-lamellar or micellar (preferably non-lamellar). More preferably, at least 85% and most preferably at least 95% of particles to be loaded will be non-lamellar or micellar (preferably non-lamellar), as measured by volume. This measurement may be made by, for example, laser diffraction, preferably combined with cryo-TEM or SAXS (to confirm the particle structure).

As used herein, the term "non-lamellar" is used to indicate a normal or reversed liquid crystal phase (such as a cubic or hexagonal phase) or the $L_3$ phase or any combination thereof. Where a particle is described as having a non-lamellar phase or form, this indicates that at least the internal region of the particle should adopt this form. Non-lamellar particles will generally have two distinct regions, an internal region and a surrounding surface region. The surface region, even in a "non-lamellar" particle will often be lamellar or crystalline and may be any phase ranging from a highly ordered crystalline or liquid crystal phase to a virtually orderless fluid layer. In contrast, a "lamellar" particle, as described herein is a particle having a solvent, rather than non-lamellar, core-region.

A "micellar" particle is used herein to indicate a particle having no core region (in the sense that the "core" is formed largely by the amphiphile molecules themselves) such as in an $L_2$ phase, or is a "microemulsion" particle in that it contains a core of a solvent largely immiscible with the surrounding continuous phase (e.g. an oil or oily amphiphile). Preferred micellar dispersions are $L_2$ phase dispersions.

The term "lamellar particles" is used herein to indicate vesicular particles characterised in that they comprise one or more outer lamellar bilayers of amphiphile, surrounding an inner solvent compartment where this inner solvent is largely miscible with the surrounding continuous phase.

The presence of particles of a particular phase structure (e.g. non-lamellar form) will preferably be assessed from a set of cryo-transmission electron microscopy particle images. Such images will typically show at least 30 particles, preferably they will show a sample of more than 50 and most preferably more than 100 particles. The presence of non-lamellar particles may also be assessed by X-ray scattering experiments.

The invention and the loading method of the invention provide particles with a higher loading level than is obtainable by equilibration at 37° C. Such particles have a loading of at least 130% of the level achievable by equilibration and generally between 150% and 700% of that value. Preferably the loading should be at least 200% of the level achievable by equilibration and more preferably at least 250%.

In the context of active agent loading, the terms "equilibration" or "equilibration at 37° C." as used herein may be taken to indicate a method comprising the following steps:
I) preparing a 1% (by weight) dispersion of amphiphile particles in an aqueous solvent (e.g. water or 0.9% NaCl);
II) adding excess active agent to the dispersion (e.g. 15 mg to a total volume of 3 ml to give a saturated solution)
III) incubating the sample at 37° C. for 3 days, optionally with gentle magnetic stirring (up to 300 rpm) or on a rotating table (up to 1 rpm);
IV) separating excess active agent from the dispersion (e.g. by filtration through a 5 μm filter);
V) analysing the active present in the dispersion (e.g. by optional dissolution in 10 volumes of water/acetonitrile/methanol (50/45/5) and analysis by high performance liquid chromatography); and
VI) calculating the percentage by weight of active agent incorporated relative to the total weight of amphiphile(s).

The skilled worker will have little difficulty in reproducing this method but reference may also be made to the Examples below for further details.

The period of 3 days has been chosen herein as a suitable period for providing essentially maximum loading of active agent by the equilibration method.

The loading of active agents has been found to plateau at around 1 day as is, for example, indicated in FIG. 1 attached hereto. This loading study can easily be repeated by a skilled worker for any active/particle combination. Should it thereby be discovered that 3 days is insufficient to approach maximum loading in any particular and case, a correspondingly increase the equilibration time to 5, or even 10 or more days could be made as appropriate.

As a comparison, particles of or loaded by the invention may be compared with particles loaded by equilibration by preparing particles of the invention and subjecting them (after cooling to 37° C. or preferably to room temperature and preferably after equilibration at that temperature for at least one hour) to steps IV to VI as described above. The resulting percentage loadings can then be expressed as a proportion, percentage or percentage increase, relative to the loading provided by the equilibration method. As used herein, the term "carrier capacity" is applied to the percentage weight of incorporated active agent relative to that of total amphiphile.

The temperature to which the particles must be heated in order to provide the effect of the present invention will be readily established by one of skill in the art. For example, a sample of particles dispersed in a saturated solution of active agent may be heated to a particular temperature for 4 hours and subsequently cooled (e.g. to ambient temperature). The loading level of active agent (carrier capacity) may then be analysed and compared to the loading provided by equilibration. If no, or insufficient, increase is observed then the experiment may be repeated at increased temperature. Similarly, the length of time required for loading at any particular temperature may be assessed by heating suitable samples for set times and examining any changes in loading level in comparison with an equilibrated standard. Equivalent heating experiments will also determine the effect upon particle size distribution and storage stability, using analytical tools such as high performance liquid chromatography, light scattering and cryo transmission electron microscopy.

Purely as a guide, samples will typically be heated to a temperature in the range 75 to 200° C., preferably 85 to 150° C., more preferably 96 to 140° C. The most preferred temperature range is 100 to 130° C. The heat may be supplied by any appropriate method, such as by autoclaving, baking in an oven, by electromagnetic irradiation (e.g. infra-red or microwave irradiation) and/or alternatives known in the art. Generally, where heating is to a temperature in excess of around 100° C., the dispersion will be sealed and/or pressurised to avoid excessive loss of solvent.

Typical periods of heating at an elevated temperature are relatively short and will generally be between 1 minute and 4 hours, more typically between 2 minutes and 1 hour. Periods of between 2 and 30 minutes are preferred, particularly between 5 and 20 minutes. The period may optionally include a period for temperature equilibration, typically 1-10 minutes. Longer periods may be used but, where no further or desirable benefit to the carrier capacity is found by longer heating, this will not typically be desirable.

The concentration of amphiphile in the dispersion of amphiphile particles treated by the method of the present invention is typically 0.1 to 20% by weight of dispersion. More preferably this will be 0.3 to 10% and most preferably in the range 0.5 to 7% (e.g. 1 to 5%). The exact concentration used during the heat treatment step will vary depending upon the desired final use of the loaded particles and also upon the desired particle size distribution. Heat treatment loading of the invention can provide some simultaneous control over particle size as indicated herein below.

The components of the amphiphile particles referred to herein include at least one structuring agent (an amphiphile) and will generally also include a fragmentation agent (which may also be an amphiphile, such as a surfactant, copolymer and/or protein, preferably a surfactant). In addition, the invention provides particles incorporating an active agent, which includes protein, drug, nutrient, cosmetic, diagnostic, pharmaceutical, vitamin, or dietary agents. Under some circumstances the structuring agent or fragmentation agent may also be an "active agent", in the sense of being bioactive but, as used herein, the term "active agent" does not include structuring agents, fragmentation agents or solvents forming part of the bulk composition. In one embodiment of the invention, the active agent is not a structure-forming amphiphile and is not a fragmentation agent, as described herein. In a further embodiment, the active agent is not an amphiphile.

The term structuring agents, as used herein, indicates amphiphilic agents that are capable of forming (as the major component—i.e. at greater than 50% by weight) lamellar, micellar and/or non-lamellar phase structures, optionally in the presence of other agents such as fragmentation agents. Structuring agents will be amphiphiles, having at least one polar, hydrophilic group and at least one non-polar, hydrophobic group. A wide range of structuring agents are applicable for use as all or part of the structuring agent component.

Examples of polar groups are well known (see e.g. US published patent application number 20020153509) and include anionic groups such as carboxylates, phosphonates, sulphates and sulphonates, non-ionic groups such as alcohols, polyols (eg sugars, glycerol etc) and esters, cationic groups such as quaternary ammonium compounds, pyridinium salts and quaternary phosphonium salts and zwitterionic groups such as phospholipid head groups (e.g phosphatidyl-choline, phosphatidic acid, phosphatidyl-ethanolamine, phosphoglycerol, phosphoserine, their PEGylated or mPEGylated derivatives, etc.), ammonioacetates, ammonio-alkanesulphonates and trialkylaminoalkylphosphate esters.

Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Y indicates a hydrocarbon chain having X carbon atoms and Y unsaturations. Examples particularly include caproyl (C6:0), caproyloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. An amphiphile will typically have one or two non-polar "tail" groups (mono-acyl and di-acyl lipids respectively) but may have three, four or more hydrophobic groups.

Examples of structuring agents suitable for use in the present invention include natural lipids, synthetic lipids, surfactants, and copolymers. Preferred agents are glycerides (e.g. monoglycerides, diglycerides, and triglycerides), di- and polyglycerolesters of glycerides (e.g. diglycerol monooleate, diglycerol monocaprate), natural fats and oils (e.g. soybean oil, coconut oil, corn oil, castor oil, sunflower oil), fractionated oils (e.g. fractionated coconut oil, Miglyol® (Condea)), transesterified oils (e.g. Maizine®), transesterification products of oils and PEG (e.g. ethoxylated castor oil (e.g. Cremophor® EL (BASF)), ethoxylated hydrogenated castor oil (e.g. Cremophor® RH-40 (BASF)), ethoxylated corn oil (e.g. Labrafil® M 2125 CS (Gattefossé))), acetylated monoglycerides, fatty acids (e.g. C6-C26 saturated and unsaturated fatty acids), fatty alcohols (e.g. phytantriol (3,7,11,15-tetramethyl-1,2,3-hexadecantriol)), ether lipids (e.g. monooleyl glyceryl ether), natural and synthetic phospholipids (e.g. egg lecithin, soya lecithin, hydrogenated lecithin, phosphatidyl choline, phosphatidyl ethanolamine, phosphatidyl serine, phosphatidyl glycerol, phosphatidic acid), lyso-phospholipids (e.g. lyso-lecithin, lyso-phosphatidyl choline, lyso-oleyl phosphatidyl choline), phospholipid-analogous compounds (e.g. those disclosed in U.S. Pat. No. 6,344,576), sterols and sterol derivatives (e.g. cholesterol, sitosterol, lanesterol and their esters, especially with PEG or fatty acids), galactolipids (e.g. digalactosyl diacylglycerol, monogalactosyl diacylglycerol), sphingolipids (e.g. sphingomyelin); non-ionic surfactants, in particular ethoxylated surfactants such as PEG-fatty acid mono- and diesters (e.g. of the Crodet® (Croda), Cithrol® (Croda), Nikkol® (Nikko), Myrj® (ICI) series, Solutol® HS 15 (BASF)), PEG glycerol fatty acid esters (e.g. Tagat® L and O (Goldschmidt), Glycerox® L series (Croda), Capmul® EMG (Abitec)), transesterification products of oils and PEG (e.g. of the Labrafil® (Gattefossé), Cremophor® (BASF) Crovol® (Croda) and Nikkol® HCO (Nikko) series), PEG-sorbitan fatty acid esters (e.g. Tween® 20, Tween® 80 and other polysorbates of the Tween® series (ICI)), PEG alkyl esters (e.g. of the Brij® (ICI) and Volpo® (Croda) series), PEG alkyl phenol surfactants (e.g. of the Triton X and N series (Rohm & Haas); polyglycerised fatty acids (e.g. Nikkol® Decaglyn (Nikko), Plurol® Oleique (Gattefossé)), propylene glycol fatty acid esters), propylene glycol fatty acid esters (e.g. Capryol® 90 (Gattefossé), Lutrol® OP2000 (BASF), Captex® (Abitec)), glycerol/propylene glycol fatty acid esters (e.g. Arlacel® 186 (ICI)), sorbitan fatty acid esters (e.g. of the Span® (ICI) and Crill® (Croda) series), sugar esters (e.g. of the SUCRO ESTER® (Gattefossé) and Crodesta® (Croda) series), polyoxyethylene-polyoxypropylene block copolymers (so-called poloxamers, e.g. of the Pluronic® (BASF), Synperonic® (ICI) and Lutrol® (BASF) series), copolymers of ethylene oxide and butylene oxide; anionic surfactants including fatty acid salts, bile salts (e.g. sodium cholate, sodium glycocholate, sodium taurocholate), carboxylates such as ether carboxylates, succinylated monoglycerides, mono/diacetylated tartaric acid esters of mono- and diglycerides, citric acid esters of mono- and diglycerides, glyceryl-lacto esters of fatty acids, acyl lactylates, alginate salts, propylene glycol alginate; cationic surfactants including ethoxylated amines (e.g. polyoxyethylene-15 coconut amine), betaines (e.g. N-lauryl-N,N-dimethylglycine), alkylpyridinium salts, quarternary ammonium salts such as hexadecyl triammonium bromide, decyl trimethyl ammonium bromide, cetyl trimethyl ammonium bromide; zwitterionic surfactants including trimethylammonioethylalkylphosphonates (e.g. the examples disclosed in U.S. Pat. No. 6,344,576); and all mixtures thereof. The most preferred structuring agents are glycerol and diglycerol monooleate and monolinoleate, glyceoldioleate (GDO), dioleyl phosphatidyl ethanolamine (DOPE), dioleyl phosphatidylcholine (DOPC) and phytantriol, and mixtures of these with up to 50% fatty acids, in particular oleic acid and linoleic acid, polysorbate 80 (Tween® 80), polyethylene glycol 660 12-hydroxysterate (Solutol® HS 15), or lyso-phospholipids, especially lyso-oleyl phosphatidylcholine (LOPC).

Often the structure forming agent component will contain components in the form of extracted and purified natural products and will thus contain a mixture of related compounds. Soy bean phosphatidyl choline, for example is a mixture of compounds having around 60-75% C18:2 acyl groups, around 12-16% C16:0 and the balance others. Similarly, commercial glycerol monooleate is typically at least 90% monoglyceride but contains small amounts of diglyceride and free fatty acid, with the acyl groups being over 60-90% C18:1, 5-10% saturated and the remainder largely higher unsaturated acyl groups.

A highly preferred structuring agent for use in the present invention is commercially available glycerol monooleate (GMO). As indicated above, this is largely monoglyceride with an oleoyl (C18:1) acyl chain but contains certain amounts of other compounds. These are included in the term "glycerol monooleate" or "GMO" as used herein. Commercial preparations of GMO include. GMOrphic-80 and Myverol 18-99 (available from Eastman Kodak), Rylo MG 19 and Dimodan DGMO (available from Danisco). Any of the structuring agents may be used alone or in combination with one or more other structuring agents. Other preferred structuring agents include Diglycerolmonoacyl lipids such as Diglycerolmonooleate (DGMO) and glyceroldiacyl lipids such as glyceroldioleate (GDO), as well as mixtures thereof.

As all, or preferably a portion of, the amphiphilic structuring agent component, the particles of the invention may, in particular, include at least one fatty acid or fatty acid salt component. Preferred fatty acids have between 6 and 24 carbons and particularly those corresponding to the fatty acid chains of natural lipids, including caproic, caprylic, capric, lauric, myristic, palmitic, phytanic, palmitolic, stearic, oleic, elaidic, linoleic, linolenic, arachidonic, behenic or lignoceric acids, their salts or mixtures thereof. The fatty acids may be saturated but are preferably unsaturated. The most preferred fatty acid is oleic acid. Salts of fatty acids will typically be physiologically tolerable, and for pharmaceutical applications will always be so. Preferred salts include alkali and alkaline earth metal salts such as sodium, potassium, lithium, calcium or magnesium salts as well as ammonium and alkylammonium salts. Typically, the fatty acid or fatty acid salt will be present as 0-10 wt % of the total amphiphilic component, preferably 3-7% by weight.

Particularly where the method of the present invention is used to load microemulsion "micellar" dispersions, at least a portion of the structuring agent component may be one or more oily components being largely immiscible with water. Typical oily amphiphiles have a Hydrophilic-Lipophilic Balance (HLB) of 4 or less. Preferred examples of such oily structuring agents include triglycerides, diesters of ethylene or propylene glycol, fatty acid/fatty alcohol esters and tocopherols. Where these low HLB amphiphiles are used, it will usually be necessary to include at least one surfactant type fragmentation agent, especially where the portion of oily amphiphile is high.

The fragmentation agents for use in the particles referred to herein will be at least one agent which aids the dispersal of the structuring agent particles (preferably micellar or particularly non-lamellar particles) or stabilises such particles. Typically a fragmentation agent will be a surfactant such as an amphiphilic block copolymer. A large number of surfactants and copolymers are suitable for use as all or part of the fragmentation agent for use in the present invention. Typically fragmentation agents have an HLB of at least 12, preferably at least 14.

Important fragmentation agents include natural lipids, synthetic lipids, surfactants, copolymers, proteins (in particular caseins and albumin), hydrotropes, alcohols and other additives that may facilitate fragmentation spontaneously or with the aid of externally applied forces and pressures and contribute to stabilisation. This includes also nanoparticles and combinations of polymer and nanoparticles (see e.g. WO 99/12640).

Suitable copolymers for use as fragmentation agents may have blocks comprising polyoxyalkylenes, polyvinylpyrrolidone, polyvinylacetate, polyvinylalcohol, polyesters, polyamides and/or polyalkenes. The block copolymer will comprise at least two blocks of polymer having different degrees of hydrophilicity.

Certain proteins (such as casein) are also of amphiphilic character and may be used as fragmentation agents but are not preferred.

Preferred examples of amphiphilic block copolymers are poloxamers, which comprise at least one block of polyoxyethylene and at least one block of polyoxypropylene. The most preferred fragmentation agents are poloxamer 407 (e.g. Pluronic® F127, BASF), poloxamer 188 (e.g. Pluronic® F68, BASF), poloxamer 124 (Pluronic® L44, BASF), and polysorbates 20, 60 and/or 80 (referred to herein a P20, P60 & P80 respectively—e.g. Tween® 80, ICI). Other suitable surfactants copolymers may be found in the "Handbook of Pharmaceutical Excipients" (2nd Ed., the American Pharmaceutical Association and The Pharmaceutical Press, Royal Pharmaceutical Society of Great Britain).

Other preferred fragmentation agents include polyethylene glycol lipid conjugates (e.g. PEGylated and mPEGylated phospholipids) as well as long chain alcohols and fatty acids.

Particularly preferred fragmentation agents include PEGylated castor oils (Cremophors), polysorbates (P80), any PEGylated lipids with more than about 20 PEG units per molecule, block copolymers (e.g. PEG-PPG block copolymers—poloxamers), hydrophobically modified (hf) polymers (hf polysaccharides such as hf starch, hf polyacrylates and hf cellulose derivatives), polyglycerin attached phospholipids (e.g. Coatsome EL Series from NOF), cholesterol pullulan (NOF) and 2-Methacryloyloxyethyl phosphorylcholine n-butyl methacrylate co-block polymers (PUREBRIGHT MB-37-50T and PUREBRIGHT MB-37-100T from NOF).

Since the amphiphiles for use in the method of the invention or comprised in the particles of the invention are subjected to heat treatment, it is desirable that they be stable to these conditions. Typical structuring agents will generally be sufficiently stable to avoid degradation under these conditions but certain possible fragmentation agents, such as peptides, are more temperature sensitive and are thus not preferred. All components of the particles should be stable to the conditions of heat treatment and this can be tested as described herein.

In a preferred embodiment of the present invention, the particles referred to herein have amphiphilic components comprising at least one structure forming amphiphile (component a), at least one "structure swelling" agent (component b) and at least one dispersion stabilising "polymeric" agent (component c). Components b and c will also act as fragmentation agents. In this embodiment, at least 50% by weight of the total amphiphilic components (a+b+c) should be component a. Preferably this will be 60 to 95%, more preferably 70 to 90%. Correspondingly, component b should be less than 40% by weight of a+b+c, preferably 5 to 30% and more preferably 10 to 25%. Component c should be present at less than 20%, preferably 1 to 15% and more preferably 2 to 10% of the total weight of a+b+c.

Compositions comprising components a, b and c as described herein ("ternary compositions") are highly suitable for use in the methods of the present invention and in particular are highly suitable for forming desirable non-lamellar particles for loading by the method of the invention. Such particles typically have a thermodynamically stable non-lamellar state at room temperature in an appropriate aqueous medium. Furthermore, the compositions may have favourable in vivo properties such as low haemolytic effects and low acute toxicity, thereby providing enhanced utility as carriers for active agents such as drugs and/or nutrients (see active agents indicated herein).

In the ternary amphiphilic compositions, structure forming component "a" will preferably comprise at least one lipid component such as glycolipids, diglycerides and/or phospholipids (e.g phosphatidyl ethanolamines). Naturally occurring lipids are particularly suitable but non-naturally occurring variants such as ether lipids (having a head and tail group joined by an ether bond) are also suitable. Lipids such as diacyl phosphatidyl ethanolamines, and diacylglycerols and diacyl phosphatidyl cholines are highly suitable.

In this embodiment, component a may also contain up to 10% (e.g. 1-10% by weight of this component) of at least one charged amphiphile, particularly anionic lipids (such as acyl or diacyl phosphatidyl glycerols) or fatty acid (see above). Correspondingly, 90% or more, preferably at least 95% of the component a should preferably have no net charge under neutral and/or physiological conditions, Component a when formulated alone in excess water should form a reversed non-lamellar phase, preferably a reversed hexagonal phase.

The structure swelling component "b" is generally a component which swells the lattice of the amphiphilic structure allowing it to more readily be dispersed into particulate form. This component may also facilitate structural transition, for example, from reversed cubic to hexagonal phase structures. Structure swelling agents will generally have a relatively low molecular weight (e.g. less than 2000) and are preferably components such oligoethylene oxide based surfactants. Preferred examples oligoethylene oxide based surfactants are those having between 5 and 40 ethylene oxide units bonded to a non-polar "tail" group (e.g. as an ester to a fatty acid, such as any of those described herein, or as an ether to a corresponding fatty alcohol). Preferred examples include polyoxyethylene alkylethers, polyoxyethylene sorbitan fatty acid esters (polysorbates), polyoxyethylene sterates, polyoxyethylene castor oil derivatives and polyoxyethylene lipid derivatives. Most preferred examples are TMGO-15 (Nikko), Solutol HS15 (BASF) and polysorbate 80.

The polymeric component "c" is, in general, a component which improves the stability of the dispersion, particularly as colloidal particles. Polymeric components generally have a relatively high molecular weight (e.g. greater than 2000) and will have at least one polymeric or copolymeric portion in their molecular structure. Preferred polymeric components include polyethylene oxide copolymers and lipids derivatised with polyethylene oxide, hydrophobically modified polysaccarides and amphiphilic proteins. Poloxamers as described herein are particularly suitable as the polymeric components as are PEG-substituted lipids such as PEG-glyceroldioleate, PEG-dioleoyl phosphatidyl ethanolamine (in particular DOPE-PEG2000 and DOPE PEG-5000) or PEG-dioleoyl phosphatidyl serine.

Preferred examples of polyethylene oxide copolymers are poloxamers, which comprise at least one block of polyoxyethylene and at least one block of polyoxypropylene. The most preferred of these agents are poloxamer 407 (e.g. Pluronic® F127, BASF), poloxamer 188 (e.g. Pluronic® F68, BASF), poloxamer 124 (Pluronic® L44, BASF).

In all particles referred to herein, fragmentation agent(s) will be present at a level sufficient to bring about the fragmentation of the structuring agent and/or to stabilise the particles. In some cases no fragmentation agent will be required but in others, particularly in order to disperse non-lamellar phases, fragmentation agent(s) will be necessary. The particles may form spontaneously or may require physical fragmentation such as by shearing and/or ultrasonication. It is preferable that sufficient fragmentation agent is present that the particles are physically stable.

Preferred combinations of structure forming agents and fragmentation agents include combinations of GMO, GDO, DGMO and/or DOPE with at least one of Poloxamer 407, Poloxamer 188, TMGO-15/DOPE-PEG(5000) and/or P80.

In one preferred embodiment, the particles of and for loading in the method of the present invention consist of GMO and one or more fragmentation agents (such as poloxamers), with an active agent after loading and optionally with an aqueous component.

Active agents suitable for inclusion in the methods and formulations of the present invention include human and veterinary drugs and vaccines, diagnostic agents, "alternative" active agents such as plant essential oils, extracts or aromas, cosmetic agents, nutrients, dietary supplements etc. The active agents will desirably be stable to the heat treatment loading method and the particular amphiphilic particles, temperature and heating time chosen for use in the loading method will take into account active agent stability. When suitable conditions are chosen, the active agent(s) should be stable as indicated herein above. Virtually any active agent satisfying this requirement may be used in the method and particles of the invention.

It is preferred, in order to provide the greatest increase in loading, that the active agent have a relatively low aqueous solubility. Preferably, the active agent will have a high log P (being the log to base 10 of the partition coefficient of the active agent between water and n-octanol), such as log P>2, preferably log P>2.5 and more preferably log P>3. Preferably the active agents will have a relatively low melting point, such as below 170° C., preferably below 150° C. and most preferably between 100° C. and 140° C.

Examples of suitable drugs include steroids, sparingly soluble weakly basic drugs, fibrins, statins, dipins, and azoles. Specific preferred examples of these include progesterone, testosterone, simvastatin, lovastatin, nifedipin, felodipin, nicardipin, nimodipin, itraconazole, fluconazole, miconazole, econazole, voriconazole, clotrimazole, ketoconazole, fulvestrant, fenofibrate, octreotide, undecanoate, estradiol, cortisone, hydrocortisone, 11a-hydroxyprogesterone, clofibrate gemfibrozil, bezafibrate, ciprofibrate. Some categories of active agents, such as peptides, are less preferred due to their limited heat stability in aqueous solution. Certain peptides, especially cationic and cyclic peptides, however, are more temperature stable and these are suitable for use in the invention. Octreotide is an example of a temperature stable peptide. Most preferred active agents are progesterone, ketoconazole, fulvestrant, fenofibrate, octreotide and testosterone.

Diagnostic agents include radionuclide labelled compounds and contrast agents including X-ray, ultrasound and MRI contrast enhancing agents. Nutrients include vitamins, coenzymes, dietary supplements etc. The active agents for use in the present invention will generally not be poloxamers or acylglycerols.

An active agent will frequently have an effect upon the phase behaviour of the structuring agent(s). For example, certain active agents (such as cyclosporin A) introduce greater negative curvature than some structuring agents and at high concentrations may cause the formation of highly negatively curved phases, such as the reversed micellar $L_2$ phase rather than a cubic or hexagonal liquid crystalline phase. Nonetheless, such an active agent could be formulated into, for example, a reversed hexagonal phase by formulation with a structuring agent, or a blend thereof, having a less negative spontaneous curvature. By this method, the overall mixture provides the appropriate negative curvature to allow use in the methods or compositions of the invention.

The skilled worker will be able to use standard methods to assess the degree of spontaneous curvature of any particular structuring agent (or mixture thereof) or the effect on this by including an active agent. This might be done, for example, by studies of the bulk phase behaviour of each structuring agent in water and subsequent studies with varying concentrations of active agent included. The phases can be examined by any of the methods indicated herein (e.g. polarised light, SAXS cryo-TEM etc.) and an appropriate blend of structuring agents chosen for each case. In some circumstances, where the effect of the active agent on the phase behaviour of the mixture is significant, the structuring agent(s) chosen may not provide the desired phase in themselves (e.g. may have too small or too great spontaneous curvature) but will generate this phase only when also formulated with the active agent. Similarly, the equilibrium phase may change from, for example, cubic to hexagonal liquid crystalline phase upon addition of the active agent.

The loading method of the present invention may also be used to simultaneously load active agent into amphiphilic particles and to control the particle size and size distribution. The inventors have established that average particle size is generally increased by heating in media with higher ionic strength. Typically, stable, (especially non-lamellar) particle dispersions may be formed by carrying out the heat treatment loading step at ionic strength in the range 0.1 mM to 100 mM NaCl (or ionic strength equivalent) depending upon the composition used. The precise size distribution will depend upon the composition and suitable conditions may quickly be established by reference to the methods described herein, but typically sub-micron particles are formed at low ionic strength and larger colloidal and non-colloidal particles at increasing ionic strengths.

Where small particles are required in solutions of relatively high salt concentrations (e.g. in 0.9% NaCl for injections) the particles may be formed by the heat treatment method of the invention at a low ionic strength and, after cooling, further salt(s) added to provide the desired osmolality.

In a yet further embodiment of the invention, the present inventors have further established that the particle size distribution of a formulation comprising at least one structuring agent may be further controlled by carrying out the loading method of the present invention in an aqueous medium at controlled concentration of amphiphile. In particular, small (e.g. colloidal, especially small colloidal (<0.3 μm)) particles are most easily formed at low concentration of amphiphile, such as below or around 10 wt % total amphiphile in aqueous solution Where small particles are required at relatively high concentrations of amphiphile (e.g. to minimize the total volume for injections) the particles may be formed by the methods of the invention at high dilution and, after cooling, concentrated by evaporation, ultrafiltration etc. Conversely, where larger particles are required at high dilutions (e.g. for infusion to a subject) then these may be formed by the processes described herein at high concentrations and, once cooled, diluted further.

In the methods of the invention, particles comprising a structuring agent are formed prior to one or more heat treatment cycles. This pre-formulation will typically be in the form of a dispersion and may be prepared by established methods. Methods for forming lamellar (e.g. liposomal) and micellar (including microemulsion) dispersions are well known and several methods for forming dispersions of non-lamellar phase particles are also well established, such as those indicated in the present Examples and in U.S. Pat. No. 5,531,925, WO 02/02716, WO 02/068561, WO 02/066014 and WO 02/068562. The disclosures of these and all references cited herein are hereby incorporated herein by reference.

Methods for forming dispersions of non-lamellar phase particles include adding an amphiphile/water liquid crystal phase to an aqueous solution of fragmentation agent and optionally a lipid (such as PC) and either allowing natural fragmentation of the mixture or accelerating the process with, for example, mechanical agitation, vortexing, roto-stator mixing, high-pressure homogenization, microfluidisation and/or ultrasound.

After heat-cycling enhanced loading, the particles may be concentrated (e.g. by ultrafiltration or dialysis) and/or dried, for example by spray drying, fluid bed drying or freeze drying. In the case of dried particles, the drying process may be followed by particle size enlargement through single or repeated agglomeration and granulation steps. The concentrated, dried and/or agglomerated particle formulations thus formed may be used as such or hydrated and/or dispersed to yield particle dispersions suitable for use in the delivery of active substances, especially in vivo. Such concentrated, dried and/or agglomerated particle formulations and the dispersions resulting from their re-suspension/hydration form further aspects of the present invention. Drying may be carried out in the presence of protective and/or resuspension promoting agents such as hydrophilic polymers or sugars, as is well known in the art.

In one embodiment of the invention, an initial pre-formulation, prior to heat treatment loading, is formed in which the particles will preferably be small colloidal sized particles, for example in the range 0.02 to 0.2 μm. Preferably the mean particle size for the small colloidal particles will be 0.05 to 0.15 μm in this pre-formulation.

The loaded particles of the invention will preferably have average (mean) sizes below 10 μm, more preferably below 5 μm and most preferably below 1 μm. In one embodiment, after loading by one or more heating and cooling cycles, the final particles should be in the colloidal size range. These will typically have an average (mode or preferably mean) particle size in the range 0.05 to 1 μm, preferably 0.1 to 0.8 μm (e.g. 0.2 to 0.8 μm), more preferably 0.2 to 0.6 μm (e.g. 0.3 to 0.6 μm). It is particularly important that preparations for use in intravenous administration should not contain particles in the non-colloidal range (e.g >1 μm or particularly >5 μm, and especially >10 μm, as indicated herein). For intravenous applications a preferred particle size range is 0.05 to 0.3 μm. This may be achieved by using the method of the invention, beginning with small colloidal particles as described above. Alternatively, or in addition, the particles, preferably after heat cycle loading, may be filtered in order to remove larger (e.g. non-colloidal) particles. In colloidal formulations, preferably no more than 10% of particles will be outside the range 0.05 to 10 μm, more preferably, not more than 1% will be outside this range, and most preferably no detectable (by laser diffraction) proportion of particles will be outside this range.

The particles formed or formable by the method of the invention may be used in the production of nutritional, dietary, cosmetic, diagnostic veterinary or pharmaceutical compositions by known methods using well known carriers, excipients and other ingredients. In the case of pharmaceutical compositions, the particles will be formulated with at least one pharmaceutically acceptable carrier or excipient and may be formed into tablets, capsules and so forth. The particles may also be formulated as a pre-prepared dispersion in an acceptable liquid, such as water, or dried (e.g. spray dried or freeze dried) and sealed in sterile containers for re-suspension prior to administration.

The present inventors have surprisingly established that the loading of active agent into amphiphilic compositions may be enhanced by one or more cycles of heat treatment as describe herein. A method of loading an active agent by heat cycling thus forms an aspect of the invention, as do the products formed thereby.

In this aspect of the invention, the active agent must be stable to the conditions of the heat cycling. The active agents should thus be chemically stable in aqueous environments under the conditions of heat and duration described herein. The suitability of any active agent for this aspect of the invention may be established by routine testing under the heat-cycling conditions described herein. Preferred active agents in this respect include steroids such as progesterone, adrenocortical hormones, gonadal hormones, cardiac aglycones, bile acids and sterols. Progesterone is particularly preferred.

Upon heat treatment by the method of the present invention in the presence of heat-tolerant active agents it has been noted that a loading level of several times that achieved by loading at room temperature can be generated. That is, at least twice the quantity of active agent can be incorporated into amphiphilic compositions described herein by heat treatment than can be incorporated by equilibration at room temperature. This ratio can be 3, 4 or 5 times and may be up to 6 or more with certain active agents. Furthermore, whether or not the active agent solubilised by this method is in a meta-stable state or in a truly stable dispersion or solution, the compositions loaded with up to 6 times the room temperature equilibrium level with active agent (especially steroid) have been observed to be stable to storage for at least two weeks. This offers considerable and obvious advantages in being able to provide high drug loads at while administering a small volume and low level of carrier to the subject.

The invention will be illustrated below by the following non-limiting examples and the accompanying figures in which.

Figure 7:
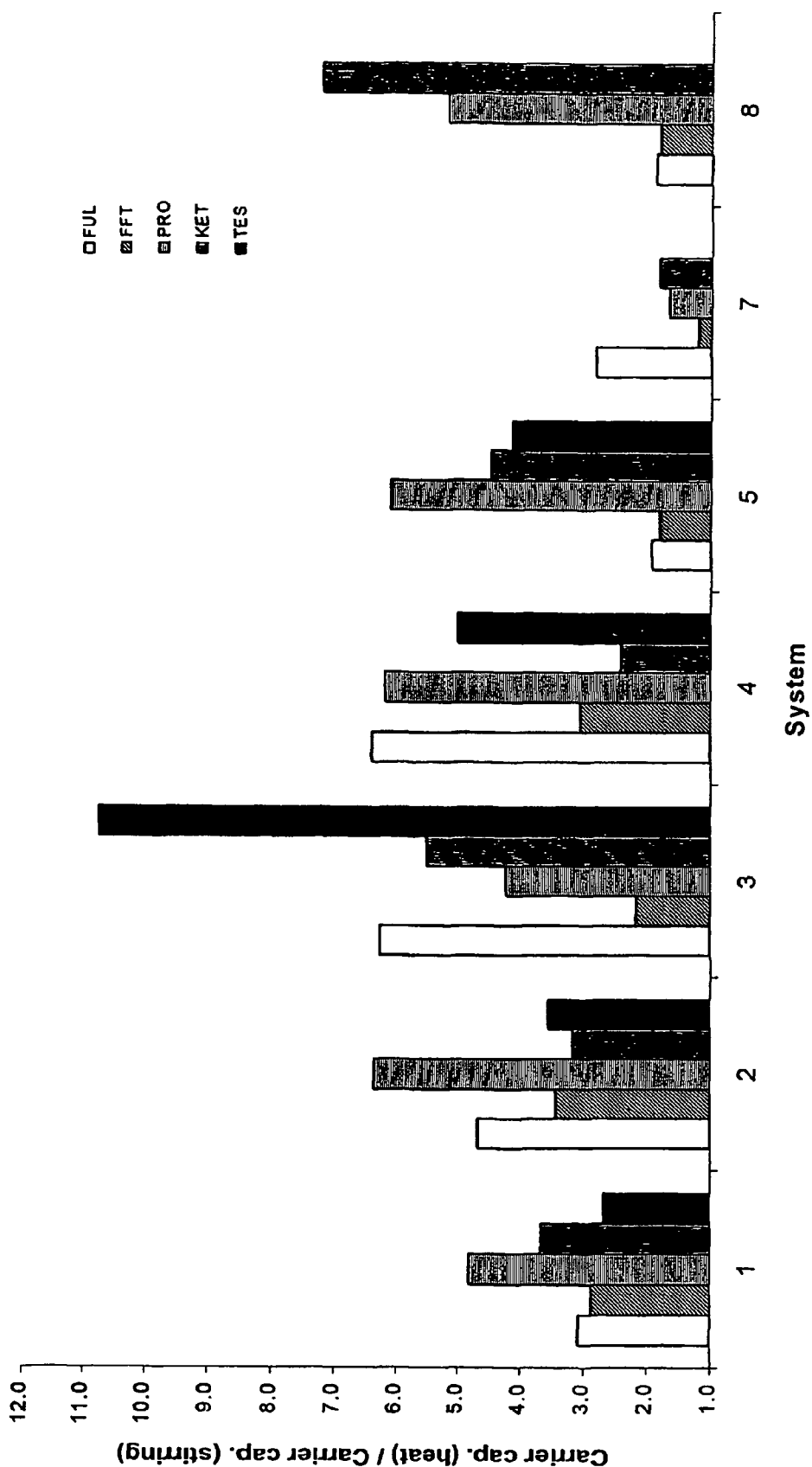
Figure 8:
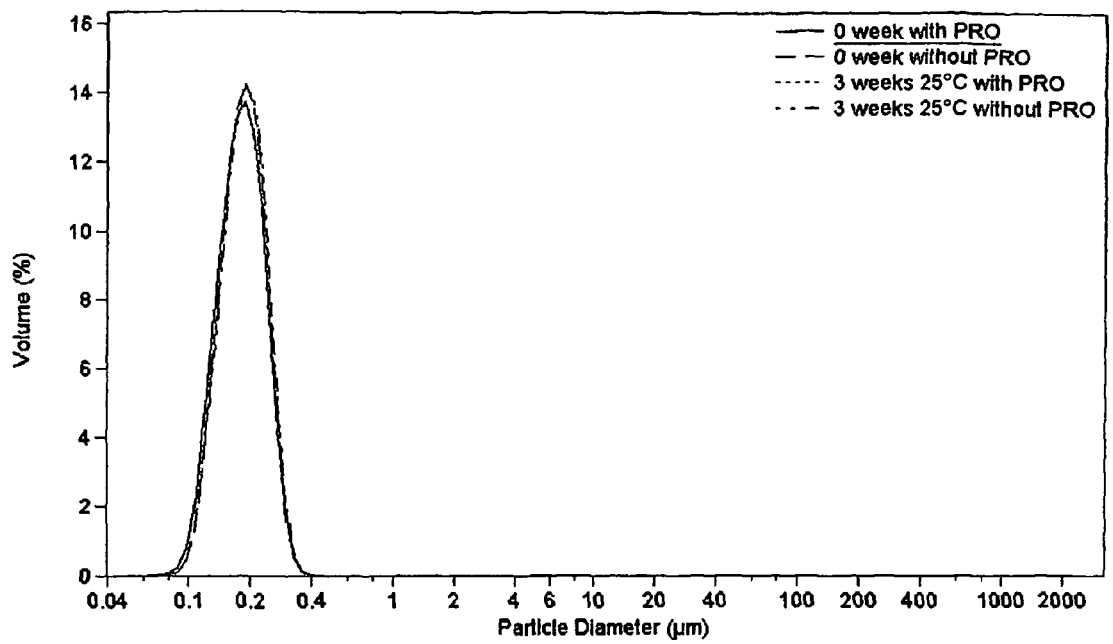
Figure 9:
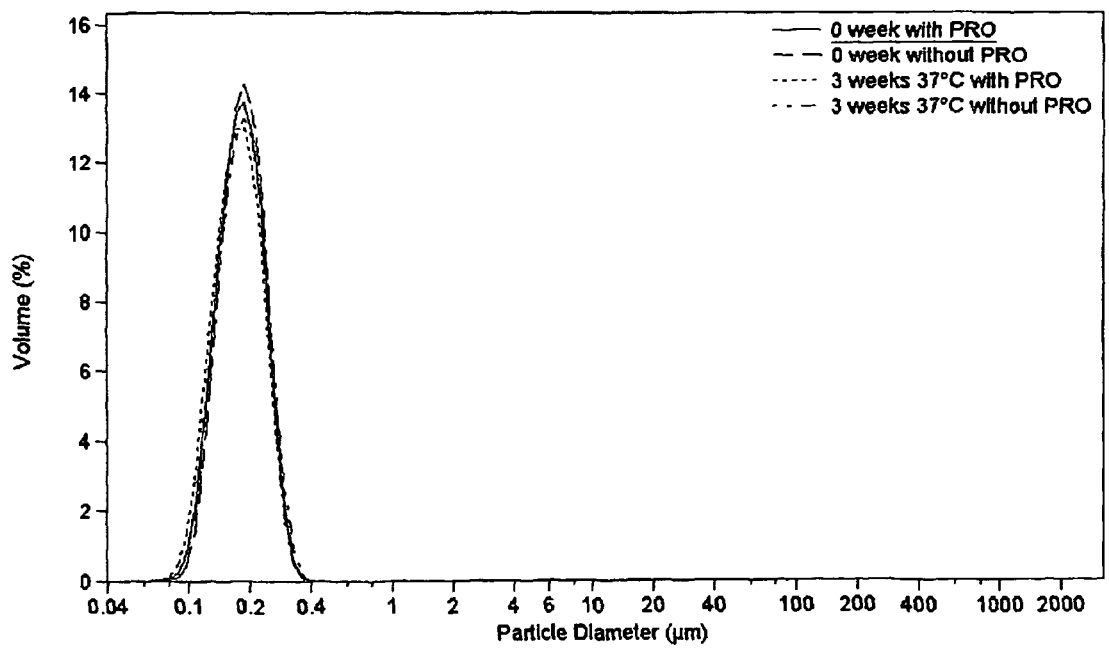

FIG. 7 shows a comparison of the relative increases in loading (carrier capacity) for 5 active agents loaded into up to 8 amphiphile dispersions by heating at 125° C. for 20 minutes in comparison with gentle stirring for 3 days at 37° C.;

FIG. 8 shows the effect upon particle size of storage at 25° C. for 3 weeks for amphiphile dispersions with and without progesterone loaded to 10% carrier capacity;

FIG. 9 shows the effect upon particle size of storage at 37° C. for 3 weeks for amphiphile dispersions with and without progesterone loaded to 10% carrier capacity;

EXAMPLES

The following materials were used in the Examples and are abbreviated as shown:
GMO glyceryl monooleate (obtained from Danisco)
OA oleic acid (Apoteket)
DGMO diglyceryl monooleate (Danisco),
GDO glyceryl dioleate (Danisco),
F127 Pluronic F127 (Sigma),
DOPE dioleoyl phosphatidylethanolamine (Avanti),
TMGO-15 PEG-15 glyceryl monooleate (Nikko),
DGMC diglyceryl monocaprinate (Danisco),
PC soybean phosphatidylcholine,
  Epikuron 200 (Degussa),
  Maisine (Gattefossé),
CrRH40 Cremophor RH40 (BASF),
P80 Polysorbate 80 (Apoteket),
PG propylene glycol (Apoteket),
EtOH ethanol 99.5% (Kemetyl).

Example 1

Preparation of Loading Compositions

Nine different aqueous loading systems were prepared at an amphiphile concentration of 1% by weight (Table 1).

TABLE 1

Compositions of loading systems

| System | GMO | OA | DGMO | GDO | F127 | DOPE | TMGO-15 | PEG5000-DOPE | DGMC | PC | Maisine | Cr RH40 | P80 | PG | EtOH | water |
|---|---|---|---|---|---|---|---|---|---|---|---|---|---|---|---|---|
| 1 | 0.9 | — | — | — | 0.1 | — | — | — | — | — | — | — | — | — | — | 99 |
| 2 | 0.86 | 0.04 | — | — | 0.1 | — | — | — | — | — | — | — | — | — | — | 99 |
| 3 | — | — | 0.54 | 0.36 | 0.1 | — | — | — | — | — | — | — | — | — | — | 99 |
| 4 | — | 0.025 | — | — | — | 0.8 | 0.15 | 0.025 | — | — | — | — | — | — | — | 99 |
| 5 | — | — | 1 | — | — | — | — | — | — | — | — | — | — | — | — | 99 |
| 6 | — | — | — | — | — | — | — | — | 1 | — | — | — | — | — | — | 99 |
| 7 | — | — | — | — | — | — | — | — | — | 1 | — | — | — | — | — | 99 |
| 8 | — | — | — | — | — | — | — | — | — | — | 0.45 | 0.54 | — | 0.13 | 0.13 | 98.75 |
| 9 | — | — | — | — | — | — | — | — | — | — | — | — | 1 | — | — | 99 |

Predispersions of systems 1-3 were prepared by dropwise adding molten amphiphile mixture to water after which the dispersions were allowed to equilibrate for about 1 day. Predispersions of systems 4, 5, and 7 were prepared by swelling the amphiphiles in water and "freeze-thaw" cycling the mixture three times, including freezing at −85° C. and thawing under vigorous stirring and shaking at ambient temperature. All predispersions were homogenized in a microfluidizer at high pressure (350 bar) for 15 min at room temperature. The dispersions were then autoclaved at 125° C. for 20 minutes and were allowed to cool to ambient temperature before further use. Final dispersions of systems 6, 8, and 9 were prepared by adding amphiphile (and cosolvent) to water and allowing the dispersions to equilibrate for at least 6 hours.

Example 2

Loading of Progesterone 15 mg of progesterone (PRO, Sigma) was added to vials each containing 3 ml of dispersion systems 1, 2, 3, 4, 5, 7, 8 (see Table 1), respectively. Four samples of each composition were prepared and water samples were prepared as a reference. Two samples of each composition were equilibrated at 37° C. for three days by gentle stirring on a rotating table. The remaining samples were heat treated by autoclavation at 125° C. for 20 minutes and were allowed to temperature equilibrate at 37° C. for at least one hour before further processing. Undissolved progesterone was separated from the dispersions by filtration through a 5 µm cutoff hydrophilic filter. The dispersions were dissolved by diluting ten times with a 50/45/5 mixture of water/acetonitrile/methanol.

Analysis of progesterone was performed on a binary HPLC pump equipped with an autosampler, a degasser and a variable-wavelength UV-VIS detector. A HiChrom ACE-5 CN column (50*4.6 mm) with 5 µm particles was used at ambient temperature.

Progesterone was eluted using a binary gradient from solvent A: 0.02% $H_3PO_4$ in water and B: acetonitrile. The gradient composition was: time$_0$ ($t_0$)=25% B, $t_4$=65% B, $t_5$=25% B and $t_6$=25% B. The flow rate was 1.5 mL/min and UV detection was performed at 254 nm.

100 µL of a sample was diluted with 900 µL of sample solvent, water/acetonitrile/methanol (50:45:5), for samples of low concentrations, and further diluted 10 times for high concentration samples. A 20 µL aliquot was injected on the HPLC.

Quantification of progesterone peaks was performed by comparing the peak area of a sample with a linear regression of calibration samples with known concentrations (0.025-200 µg/mL) mixed in sample solvent.

Figure 1:
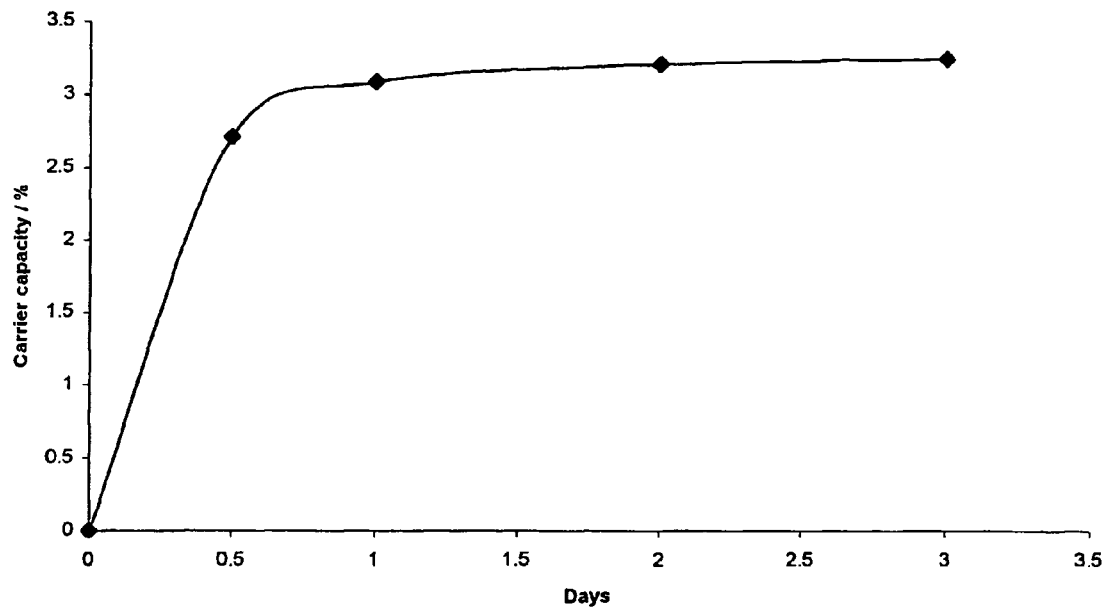
FIG. 1 shows the loading of progesterone into amphiphile particles by equilibration over 3 days.

A loading time study was performed for the constant temperature (37° C.) loading procedure and it was concluded that plateau loading was achieved after about 1 day (FIG. 1).

Figure 2:
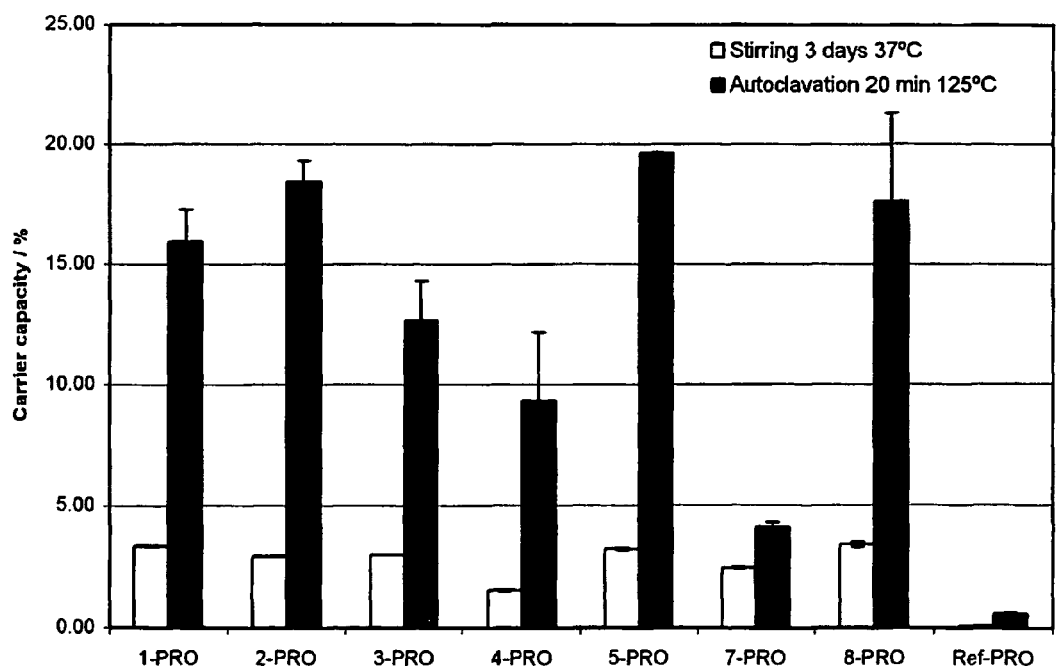
FIG. 2 shows the increase in loading (carrier capacity) when progesterone (PRO) is loaded into each of 8 amphiphile dispersions by heating at 125° C. for 20 minutes in comparison with gentle stirring for 3 days at 37° C.

The resulting loading data were presented as "carrier capacity" (FIG. 2, Table 2), which is defined as the weight percentage loaded progesterone per amphiphile (i.e. excluding the solvent).

TABLE 2

Loading of progesterone

| System | Carrier capacity/% Stirring 3 days 37° C. | Stdev | Carrier capacity/% Autoclavation 20 min 125° C. | Stdev | Relative increase | Increase (%) |
|---|---|---|---|---|---|---|
| 1-PRO | 3.32 | 0.02 | 15.96 | 1.34 | 4.8 | 381 |
| 2-PRO | 2.90 | 0.02 | 18.45 | 0.86 | 6.4 | 537 |
| 3-PRO | 2.99 | 0.01 | 12.65 | 1.65 | 4.2 | 323 |
| 4-PRO | 1.51 | 0.02 | 9.34 | 2.82 | 6.2 | 520 |
| 5-PRO | 3.21 | 0.05 | 19.64 | 0.01 | 6.1 | 512 |
| 7-PRO | 2.43 | 0.03 | 4.10 | 0.21 | 1.7 | 69 |
| 8-PRO | 3.39 | 0.11 | 17.61 | 3.71 | 5.2 | 419 |
| Ref-PRO | 0.09 | 0.00 | 0.60 | 0.02 | | | where stdev is the standard deviation, and increase and relative increase refer to the increase in carrier capacity by heat treatment over constant temperature stirring.

Example 3

Loading of Fenofibrate 15 mg of fenofibrate (FFT, Sigma) was added to vials containing each 3 ml of dispersion systems 1-8 (see Table 1), respectively. The samples were treated in the same way as described in Example 2.

Analysis of fenofibrate was performed similar to described in Example 2 with the following exceptions: A HiChrom ACE-5 C18 column (50*4.6 mm) with 5 µm particles was used at ambient temperature. Fenofibrate was eluted in isocratic mode using a mobile phase consisting of 0.02% $H_3PO_4$ in water—acetonitrile (20:80, v/v). The flow rate was 1.5 mL/min and UV detection was performed at 300 nm.

Figure 3:
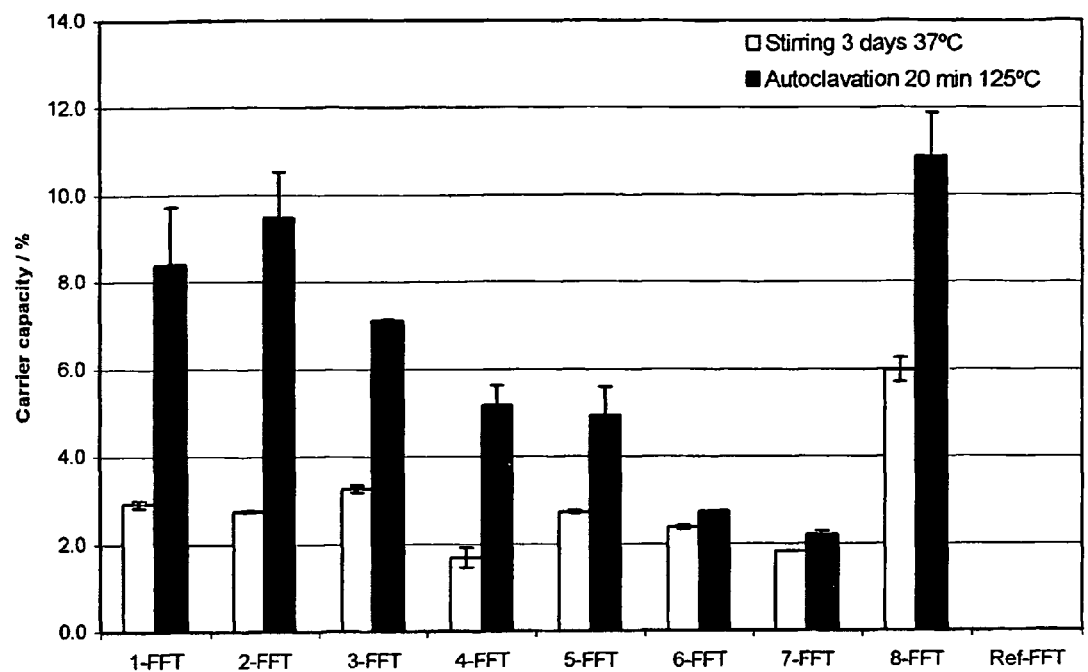
FIG. 3 shows the increase in loading (carrier capacity) when fenofibrate (FFT) is loaded into each of 8 amphiphile dispersions by heating at 125° C. for 20 minutes in comparison with gentle stirring for 3 days at 37° C.

The resulting carrier capacities are presented in FIG. 3 and Table 3.

TABLE 3

Loading of fenofibrate

| System | Carrier capacity/% Stirring 3 days 37° C. | stdev | Carrier capacity/% Autoclavation 20 min 125° C. | stdev | Relative increase | Increase (%) |
|---|---|---|---|---|---|---|
| 1-FFT | 2.9 | 0.09 | 8.41 | 1.32 | 2.9 | 188 |
| 2-FFT | 2.8 | 0.03 | 9.47 | 1.05 | 3.4 | 244 |
| 3-FFT | 3.3 | 0.08 | 7.12 | 0.04 | 2.2 | 118 |
| 4-FFT | 1.7 | 0.23 | 5.16 | 0.46 | 3.1 | 207 |
| 5-FFT | 2.7 | 0.04 | 4.94 | 0.66 | 1.8 | 81 |
| 6-FFT | 2.4 | 0.04 | 2.74 | 0.02 | 1.2 | 16 |
| 7-FFT | 1.8 | 0.01 | 2.19 | 0.08 | 1.2 | 21 |
| 8-FFT | 6.0 | 0.28 | 10.88 | 0.99 | 1.8 | 82 |
| Ref-FFT | 0.0 | 0.00 | 0.02 | 0.00 | | | where stdev is the standard deviation, and increase and relative increase refer to the increase in carrier capacity by heat treatment over constant temperature stirring.

Example 4

Loading of Fulvestrant 15 mg of fulvestrant (FUL) was added to vials containing each 3 ml of dispersion systems 1-5 and 7-9 (see Table 1), respectively. The samples were treated in the same way as described in Example 2.

Analysis of fulvestrant was performed similar to described in Example 2 with the following exceptions: A HiChrom ACE-5, C18, 5 μm, column (50*3.0 mm) with precolumn (10*3.0 mm) was used at ambient temperature. Fulvestrant was eluted using a binary gradient from solvent A: 0.02% $H_3PO_4$ in water and solvent B: acetonitrile. The gradient composition was: time$_0$ ($t_0$)=50% B, $t_3$=80% B, $t_4$=80% B, $t_{4.1}$=50% B and $t_7$=50% B. The flow rate was 0.7 mL/min and UV detection was performed at 280 nm.

Figure 4:
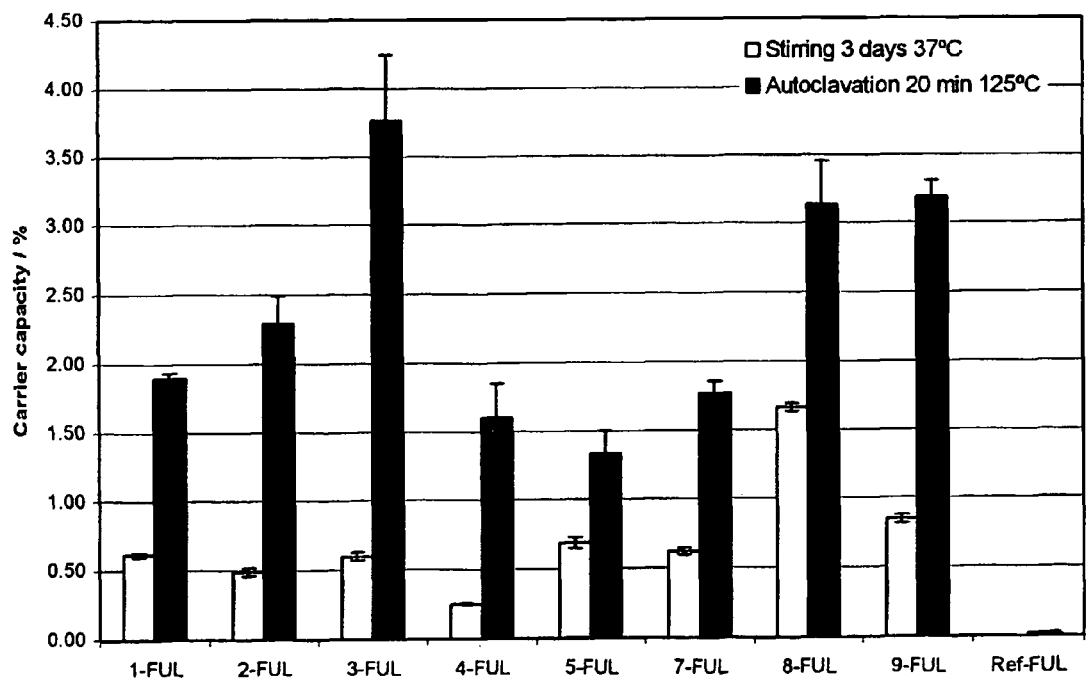
FIG. 4 shows the increase in loading (carrier capacity) when fulvestrant (FUL) is loaded into each of 8 amphiphile dispersions by heating at 125° C. for 20 minutes in comparison with gentle stirring for 3 days at 37° C.

The resulting carrier capacities are presented in FIG. 4 and Table 4.

TABLE 4

Loading of fulvestrant

| System | Carrier capacity/% Stirring 3 days 37° C. | stdev | Carrier capacity/% Autoclavation 20 min 125° C. | stdev | Relative increase | Increase (%) |
|---|---|---|---|---|---|---|
| 1-FUL | 0.62 | 0.02 | 1.90 | 0.04 | 3.1 | 208 |
| 2-FUL | 0.49 | 0.03 | 2.29 | 0.20 | 4.7 | 368 |
| 3-FUL | 0.60 | 0.03 | 3.76 | 0.48 | 6.3 | 527 |
| 4-FUL | 0.25 | 0.01 | 1.60 | 0.25 | 6.4 | 541 |
| 5-FUL | 0.69 | 0.04 | 1.34 | 0.16 | 1.9 | 94 |
| 7-FUL | 0.62 | 0.02 | 1.77 | 0.09 | 2.8 | 185 |
| 8-FUL | 1.66 | 0.03 | 3.14 | 0.32 | 1.9 | 89 |
| 9-FUL | 0.85 | 0.03 | 3.19 | 0.12 | 3.8 | 277 |
| Ref-FUL | 0.00 | 0.00 | 0.02 | 0.00 | | | where stdev is the standard deviation, and increase and relative increase refer to the increase in carrier capacity by heat treatment over constant temperature stirring.

Example 5

Loading of Ketoconazole 15 mg of ketoconazole (KET, Recordati) was added to vials containing each 3 ml of dispersion systems 1-8 (see Table 1), respectively. The samples were treated in the same way as described in Example 2.

Analysis of ketoconazole was performed similar to described in Example 2 with the following exceptions: A HiChrom ACE-3 C18 column (100*3.0 mm) with 3 μm particles was used at 45° C. Ketoconazole was eluted using a binary gradient from solvent A: tetrabytulammonium hydrogensulfate, 3.4 g/L in water and B: acetonitrile. The gradient composition was: time 0 ($t_0$)=10% B, $t_{14}$=65% B, $t_{16}$=65% B, $t_{18}$=10% B and $t_{24}$=10% B. The flow rate was 0.65 mL/min and UV detection was performed at 225 nm.

Figure 5:
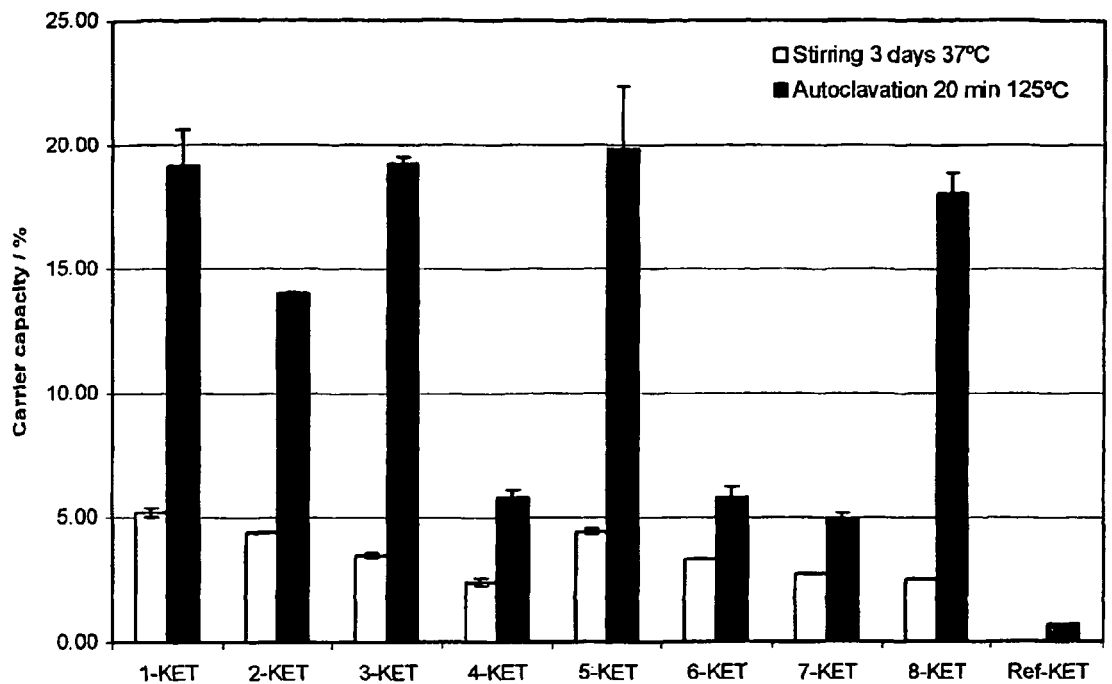
FIG. 5 shows the increase in loading (carrier capacity) when ketoconazole (KET) is loaded into each of 8 amphiphile dispersions by heating at 125° C. for 20 minutes in comparison with gentle stirring for 3 days at 37° C.

The resulting carrier capacities are presented in FIG. 5 and Table 5.

TABLE 5

Loading of ketoconazole

| System | Carrier capacity/% Stirring 3 days 37° C. | stdev | Carrier capacity/% Autoclavation 20 min 125° C. | stdev | Relative increase | Increase (%) |
|---|---|---|---|---|---|---|
| 1-KET | 5.21 | 0.18 | 19.16 | 1.46 | 3.7 | 268 |
| 2-KET | 4.41 | 0.01 | 14.01 | 0.06 | 3.2 | 218 |
| 3-KET | 3.49 | 0.10 | 19.25 | 0.28 | 5.5 | 452 |
| 4-KET | 2.40 | 0.14 | 5.82 | 0.30 | 2.4 | 143 |
| 5-KET | 4.43 | 0.10 | 19.85 | 2.49 | 4.5 | 348 |
| 6-KET | 3.32 | 0.01 | 5.82 | 0.42 | 1.8 | 75 |
| 7-KET | 2.72 | 0.02 | 4.96 | 0.22 | 1.8 | 83 |
| 8-KET | 2.50 | 0.01 | 18.07 | 0.81 | 7.2 | 624 |
| Ref-KET | 0.02 | 0.00 | 0.69 | 0.01 | | | where stdev is the standard deviation, and increase and relative increase refer to the increase in carrier capacity by heat treatment over constant temperature stirring.

Example 6

Loading of Testosterone 15 mg of testosterone (TES, Fluka) was added to vials containing each 3 ml of dispersion systems 1-2, 4-7 and 9 (see Table 1), respectively. The samples were treated in the same way as described in Example 2.

Analysis of testosterone was performed similar to described in Example 2 with the following exceptions: A HiChrom ACE-5, C18, 5 µm, column (50*3.0 mm) with precolumn (10*3.0 mm) was used at ambient temperature. Testosterone was eluted using a binary gradient from solvent A: 0.02% $H_3PO_4$ in water and solvent B: acetonitrile. The gradient composition was: $time_0$ ($t_0$)=40% B, $t_2$=70% B, $t_3$=70% B, $t_{3.1}$=40% B and $t_6$=40% B. The flow rate was 0.7 mL/min and UV detection was performed at 245 nm.

Figure 6:
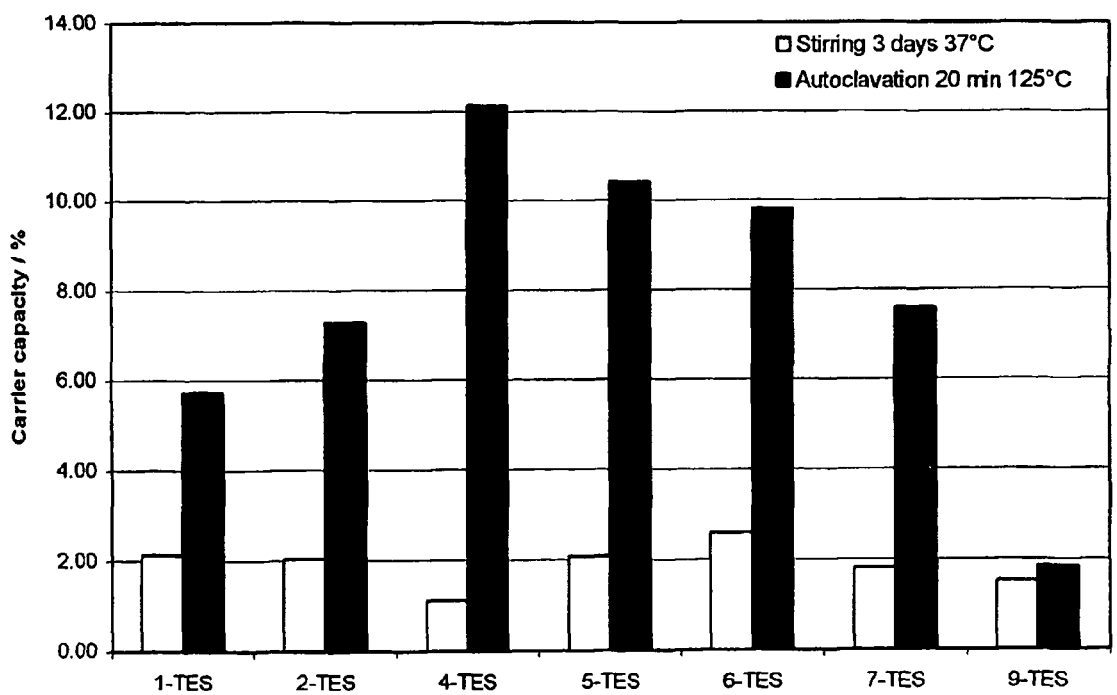
FIG. 6 shows the increase in loading (carrier capacity) when testosterone (TES) is loaded into each of 8 amphiphile dispersions by heating at 125° C. for 20 minutes in comparison with gentle stirring for 3 days at 37° C.

The resulting carrier capacities are presented in FIG. 6 and Table 6.

TABLE 6

Loading of testosterone

| System | Carrier capacity/% Stirring 3 days 37° C. | stdev | Carrier capacity/% Autoclavation 20 min 125° C. | stdev | Relative increase | Increase (%) |
|---|---|---|---|---|---|---|
| 1-TES | 2.14 | 0.03 | 5.74 | 4.73 | 2.7 | 168 |
| 2-TES | 2.05 | 0.05 | 7.28 | 5.40 | 3.6 | 256 |
| 4-TES | 1.13 | 0.02 | 12.14 | 1.52 | 10.8 | 976 |
| 5-TES | 2.08 | 0.05 | 10.42 | 2.71 | 5.0 | 401 |
| 6-TES | 2.59 | 0.03 | 9.81 | 2.39 | 3.8 | 278 |
| 7-TES | 1.82 | 0.01 | 7.58 | 0.91 | 4.2 | 316 |
| 9-TES | 1.53 | 0.01 | 1.86 | 0.26 | 1.2 | 22 |
| Ref-TES | 0.36 | 0.00 | 0.38 | 0.01 | 1.0 | -2 | where stdev is the standard deviation, and increase and relative increase refer to the increase in carrier capacity by heat treatment over constant temperature stirring.

In FIG. 7 the relative increase in carrier capacity by heat treatment loading over constant temperature stirring loading is summarized (data extracted from Examples 2-6).

Example 7

Effect of Heat Treatment on Loading of Octreotide

Octreotide at a concentration of 200 µg/ml was added to 5% amphiphile analogues of loading system 3 (water content 95%). One set of samples were equilibrated at room temperature for 1 day, while another set was autoclaved at 125° C. for 20 minutes. The ocreotide concentration was determined by HPLC using a size exclusion column coupled to a UV detector.

The heat treatment increased the portion of carrier-bound drug (Table 6).

TABLE 6

Effect of heat treatment on carrier-bound fraction of octreotide (loading system 3)

| Treatment | % bound octreotide |
|---|---|
| 1 day at room temperature | 18.07 |
| After Autoclavation 20 min | 30.04 |

Example 8

Loading and Time Effects on Dispersion Particle Size Distributions

Loading systems 1-4 generally are very stable to long term storage, and loading with active substance does not appear to affect this feature. Loading of progesterone in System 2 (10% by weight per amphiphile) does not affect the particle size distribution—neither the loading process itself, nor the stability over three weeks time (FIGS. 8 and 9).

Example 9

Stability of Progesterone to Heat Treatment

The steroid hormone progesterone is dissolved in water at a level of 1% by weight. The solution is subsequently heated to 120° C. in an autoclave for 20 minutes and cooled to room temperature. The solution is concentrated by freeze-drying and the residue analysed for breakdown products by gas chromatography mass spectrometry.

Example 10

Higher Loading by Heat Treatment

Pre-formulations were prepared, including the fatty acid oleic acid, by the following method.
  a) An initial melt was prepared containing GMO (85.5%), oleic acid (4.5%) and Lutrol F127 (10%). To 9 g of water under mechanical stirring was added 1 g of the molten mixture to form a coarse dispersion.
  b) The coarse dispersion was homogenised with a microfluidiser at 345 bar.
  c) The dispersion was heated to 120° C. for 20 minutes and cooled to room temperature.

The steroid hormone progesterone was incubated with the cubic particles formed in steps a) to c), at room temperature. The equilibrium loading level was 3% by weight.

The above method was repeated by the active agent progesterone was included in the aqueous phase prior to the homogenisation and heat treatment steps. The loading level was again examined and established to be 18 wt %. The effect upon the particle size distribution was minimal.

The composition with 18 wt % progesterone generated above was stored at room temperature for 14 days. No degradation of the composition or decrease in the loading level was observed after this time.

The invention claimed is:

1. A method for the production of amphiphile particles having incorporated therein at least one active agent, said method comprising
   (i) forming a dispersion of particles comprising at least one amphiphilic structuring agent and a solution of at least one active agent;
   (ii) heating said dispersion to a temperature in the range of 96° C. to 140° C.; and
   (iii) cooling to around ambient temperature thereby forming amphiphilic particles;
   wherein the active agent is incorporated into said particles to at least 130% of the maximum provided by a reference sample, wherein the reference sample is formed by equilibrating a dispersion of particles in a solution of at least one active agent at 37° C. for up to 3 days.

2. A method as claimed in claim 1 wherein said particles are colloidal.

3. A method as claimed in claim 1 wherein said heating is for a period of between 1 minute and 4 hours.

4. A method as claimed in claim 1 wherein, prior to incorporation of said active agent, at least 75% by volume of said particles are of non-lamellar or micellar phase.

5. A method as claimed in claim 1 wherein, after incorporation of said active agent, at least 75% by volume of said particles are of non-lamellar or micellar phase.

6. A method as claimed in claim 1 wherein, before incorporation of said active agent, the equilibrium form of the particles is non-lamellar or micellar.

7. A method as claimed in claim 1 additionally comprising drying the amphiphile particles having incorporated therein at least one active agent.

* * * * *